| United States Patent [19] | [11] Patent Number: 4,849,354 |
| Takayama et al. | [45] Date of Patent: Jul. 18, 1989 |

[54] PROCESS FOR PRODUCING MENAQUINONE-4

[75] Inventors: Kenichiro Takayama, Atsugi; Yukoh Arai, Susono; Susumu Tomohiro; Shizuko Shirasuna, both of Shizuoka, all of Japan

[73] Assignee: Kyowa Hakko Kogyo Co., Ltd, Tokyo, Japan

[21] Appl. No.: 863,008

[22] Filed: May 14, 1986

[30] Foreign Application Priority Data

May 20, 1985 [JP] Japan ................................ 60-107922

[51] Int. Cl.$^4$ ........................... C12P 7/66; C12P /104
[52] U.S. Cl. .................................. 435/133; 435/170; 435/822; 435/830; 435/843
[58] Field of Search ............... 435/133, 830, 843, 822, 435/170

[56] References Cited

PUBLICATIONS

Tani et al., *J. Ferment. Technol.*, vol. 62, pp. 321–327, (1984).
Collins et al., *Microbiol. Rev.*, 1981, vol. 45, pp. 316–354.
Bergey's Manual of Systematic Bacteriology, 1984, vol. 1, Williams and Wilkins.

*Primary Examiner*—Charles F. Warren
*Assistant Examiner*—Irene Marx
*Attorney, Agent, or Firm*—Fitzpatrick, Cella, Harper & Scinto

[57] ABSTRACT

Menaquinone-4 is produced by cultivating in culture media a microorganism belonging to the genus Corynebacterium Arthrobactor, Brevibacterium, Microbacterium, Cutobacterium, Auteobacterium or Flavobacterium which produces menaquinone-4 and recovering the same.

2 Claims, No Drawings

PROCESS FOR PRODUCING MENAQUINONE-4

BACKGROUND OF THE INVENTION

The present invention relates to a process for producing menaquinone-4 (referred to as MK-4 hereinafter) represented by the following formula:

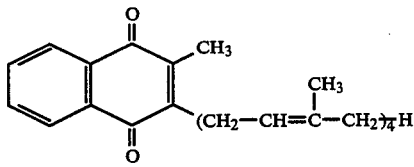

MK-4 is vitamin $K_2$-4 taking part in blood coagulation and control of calcium metabolism of a living body.

Menaquinones contained in bacteria have been thoroughly studied from the taxonomical viewpoint, and summarized by M. D. Collins and D. Jones (Microbiol. Rev., 45: 316–354, 1981). However bacteria containing a considerable amount of MK-4 as the main menaquinone have not been found. Recently, production of MK-4 by *Flavobacterium meningosepticum* as a Gram-negative bacterium has been reported by Tani et al (J. Ferment. Technol., 62: 321–327, 1984).

Improvement in industrial production of MK-4 has been required. The present inventors have studied about production of MK-4 by fermentation of microorganisms and have found microorganisms capable of producing MK-4 in good yield other than *Flavobacterium meningosepticum*.

SUMMARY OF THE INVENTION

The present invention relates to a process for producing MK-4 by using a microorganism belonging to the genus Corynebacterium, Brevibacterium, Microbacterium, Curtobacterium, Aureobacterium or Gram-positive Flavobacterium.

DETAILED DESCRIPTION OF THE INVENTION

The present invention provides a process for producing MK-4 by cultivating a microorganism belonging to the genus Corynebacterium, Brevibacterium, Microbacterium, Curtobacterium, Aureobacterium or Gram-positive Flavorbacterium and being capable of producing MK-4 in a nutrient medium, accumulating MK-4 in the culture broth, and recovering MK-4 therefrom.

Any microorganism can be used in this invention, so far as it is a microorganism belonging to the genus Corynebacterium, Brevibacterium, Microbacterium, Curtobacterium, Aureobacterium or Gram-positive Flavobacterium and being capable of producing MK-4. Specifically, *Arthrobacter nicotranae* ATCC 14929, *Corynebacterium aquaticum* ATCC 14665, *Corynebacterium choliniphilum* NRRL B-11157, *Corynebacterium murisepticum* ATCC 21374, *Microbacterium lacticum* ATCC 8180, *Microbacterium imperiale* (former *Flavobacterium imperiale*) ATCC 8365, *Microbacterium arborescens* (former *Brevibacterium arborescens*) ATCC 4358, *Curtobacterium citreum* (former *Brevibacterium citreum*) ATCC 15828, *Aureobacterium testaceum* (former *Brevibacterium testaceum*) ATCC 15829, *Brevibacterium fuscum* IFO12127, *Brevibacterium linens* ATCC 9175, *Flavobacterium marinotypicum* ATCC 19260, *Flavorbacterium flavescens* ATCC 8315, *Flavobacterium dehydrogenans* ATCC 13930, etc. are mentioned. Those skilled in the art will appreciate that *Corynebacterium liquefaciens* is also commonly classified as *Arthrobacter nicotianae*, and thus, may also be referred to by that name. This is illustrated in the prior art, for example, in Bergey's Manual of Systematic Bacteriology, Vol. 2, 1297, 1313 and Stackebrandt, *Sys. Appln. Microbiol.*, Vol. 4 (1983) 470: 86.

Bacteriological properties of these bacterial species are disclosed in Bergey's Manual, 7th edition (1957) and 8th edition (1974); Yamada and Komagata: J. Gen. Appl. Microbiol., 18: 399–416 (1972), etc.

A carotenoid pigment-producing strain belonging to the genus Corynebacterium or Arthrobacter and being capable of producing MK-4 is also preferably used in the present invention.

The carotenoid pigment-producuing strain can be obtained by subjecting a mutation treatment to a microorganism capable of producing MK-4, and deriving a carotenoid pigment-producing strain therefrom.

The mutation treatment is carried out according to conventional mutation procedures, for example, by ultraviolet ray irradiation and by chemical treatment using N-methyl-N'-nitro-N-nitrosoguanidine (NTG), nitrous acid, etc.

Suitable carotenoid pigment-producing strains are those capable of accumulating at least 10 mg/l carotenoid in a culture broth in an ordinary medium under ordinary culture conditions. Specifically, *Arthrobacter nicotiane* KS-8-18 derived from *Arthrobacter nicotianae* ATCC 14929 capable of producing MK-4 is mentioned.

Practical embodiment of constructing *Arthrobacter nicotianae* KS-8-18 is described in Example 1.

Any of synthetic medium and natural medium can be used in the present invention, so far as it appropriately contains a carbon source, a nitrogen source, inorganic matters, and other nutrients.

As the carbon source, glucose, sucrose, maltose, glycerol, sorbitol, mannitol, molasses, organic acids, fatty acids, etc. can be used alone or in combination. As the nitrogen source, ammonium sulfate, ammonium nitrate, ammonium chloride, ammonium phosphate, urea, ammonia, amines, peptone, polypeptone, yeast extract, meat extract, casein hydrolyzate, corn steep liquor, soya bean meal, etc. can be used alone or in combination. As inorganic matters, potassium dihydrogen phosphate, potassium monohydrogen phosphate, magnesium phosphate, magnesium sulfate, sodium chloride, ferrous sulfate, manganese sulfate, calcium carbonate, etc. can be used. As other trace elements, various vitamins, for example, thiamine, nicotinic acid, biotin, pantothenic acid, etc. can be used.

Sometimes, the yield of MK-4 is increased by adding a precursor substance for MK-4 biosynthesis and its related substances such as shikimic acid, 1,4-naphthoquinone and 2-methyl-1,4-naphthoquinone (vitamin $K_3$).

Cultivation is carried out under aerobic conditions, for example, by shaking culture, aerated stirring culture, etc. Suitable temperature is 20° to 40° C., preferably 25° to 35° C., and pH of the medium is kept at 5 to 9, preferably about 7.

To control the pH of the medium, aqueous ammonia, sodium hydroxide, potassium hydroxide, calcium carbonate, magnesium phosphate, urea, etc. are used.

Under these conditions, cultivation is usually continued for 3 to 7 days. MK-4 is accumulated both in the culture medium and within the microbial cells, mostly within the cells.

When the yield of MK-4 reaches the maximum, the cultivation is discontinued. Then, the cells are collected by an appropriate method, and MK-4 is separated from the cells and purified.

MK-4 is isolated from the cells or the culture broth by extraction with methanol, ethanol, chloroform, etc. alone or in combination to obtain an MK-4-containing extract, and purifying MK-4 by partition extraction using an organic solvent, or column chromatography, thin layer chromatography, etc. in combination, using silica gel, alumina, Sephadex.

Quantitative determination of MK-4 in a sample utilizes high pressure liquid chromatography of reversed phase partition type, using Shimpack ODS, Zorbax ODS, Unisil QC-18, etc.

Certain specific embodiments of the present invention are illustrated by the following examples.

EXAMPLE 1

*Arthrobacter nicotianae* ATCC 14929 (parent strain capable of producing MK-4) incubated with shaking at 28° C. for 16 hours in a bouillon medium (pH 7.2) containing 1 g/dl meat extract, 1 g/dl peptone and 0.3 g/dl NaCl were collected, and washed with a 0.05M Tris-maleate buffer solution. The cells were suspended in the same buffer solution containing 200 μg/ml N-methyl-N'-nitro-N-nitrosoguanidine and incubated at 30° C. for 2 to 3 hours. Then, the cells were washed twice with the same buffer solution, and the washed cells were incubated in a bouillon medium with shaking at 28° C. for 2 hours. The cells were collected and washed once with the same buffer solution. Then, the cells were suspended in the same buffer solution to make about $10^3$ to $10^4$ cells/ml. Then, 0.1 ml of the suspension was smeared onto a minimal medium agar plate (pH 7.2) comprising 1 g/dl glucose, 0.5 g/dl ammonium chloride, 0.2 g/dl urea, 0.1 g/dl potassium dihydrogen phosphate, 0.3 g/dl dipotassium hydrogen phosphate, 1 mg/dl ferrous sulfate, 50 mg/dl magnesium sulfate, 0.4 mg/dl manganese sulfate, 0.1 mg/dl copper sulfate, 3 μg/dl biotin, 0.5 mg/dl vitamin $B_1$, 2 mg/dl cysteine and 2 g/dl agar, and incubated at 28° C. for 3 to 4 days. Then, colonies obviously producing red pigments as compared with the parent strain were selected as carotenoid pigment-producing mutants from the colonies. From the mutants, those having maximal capability of producing MK-4 were selected and designated *Arthrobacter nicotianae* KS-8-18.

*Arthrobacter nicotianae* KS-8-18 was deposited on May 15, 1985 with Fermentation Research Institute (FRI), Agency of Industrial Science and Technology as the accession number FERM P-8232 and transferred to the deposition under Budapest Treaty on Apr. 24, 1986 as the accession number FERM BP-1022.

EXAMPLE 2

*Microbacterium lacticum* ATCC 8180 was used as a microorganism.

Slant culture on a bouillon agar medium at 30° C. for 24 hours were inoculated in a 2 l-Erlenmeyer flask provided with baffles containing 300 ml of a medium (pH 7.2) comprising 5% glycerol, 1% peptone, 0.5% yeast extract, 1% corn steep liquor, 0.01% magnesium sulfate and 0.002% ferrous sulfate, as sterilized with steam at 120° C. for 15 minutes, and separately sterilized calcium carbonate was added thereto to make 2% concentration. Then, cultivation was carried out at 30° C. with shaking at 200 rpm for 24 hours, and then the culture broth was inoculated as a seed culture into a 5 l-jar fermenter containing 3 l of the medium having the same composition as mentioned above, as sterilized with steam at 120° C. for 15 minutes, and cultivated at a temperature of 30° C. and an aeration rate of 2 vvm with agitation at 600 rpm. The day after, glycerol and peptone were added thereto to make 3% concentraton and 0.5% concentration, respectively, and the pH of the culture liquor was adjusted to keep 7.0 with 2N NaOH. After 5 days, MK-4 amounted to 30 mg/l.

Then, 1 l of the culture broth was centrifuged, whereby 35 g (dry weight) of cells was obtained. The cells were extracted three times with 300 ml of methanol at 55° C. The extract was concentrated and 200 ml of hexane was added to the resulting oily matters, and the insoluble matters were filtered off. The filtrate was admixed with 5 g of silica gel, and the mixture was stirred to adsorb MK-4 on the silica gel. After washing unadsorbed matters off, MK-4 was eluted with 30 ml of ethyl acetate, and concentrated, whereby oily matters were obtained. The oily matters dissolved in an acetone solution were spotted on thin layer chromatography (TLC) plates of silica gel 60 $F_{254}$ (made by Merck) (5 sheets), and developed with benzene:ethyl acetate (9:1 v/v). Portion showing an ultraviolet absorption of Rf80 was scraped off, extracted with acetone, concentrated, and then dissolved in acetone. Then, the solution was spotted on the above-mentioned TLC plates of silica gel 60 $F_{254}$ (5 sheets) impregnated with paraffins in advance and developed with acetone:water (95:5 v/v), and a portion of Rf62 coincident with the standard product of MK-4 was scraped off, extracted with acetone, and concentrated, whereby 24 mg of MK-4 was obtained. Melting point of the thus obtained substance was 35.1° C. By mass spectrum and nuclear magnetic resonance spectrum, the thus obtained substance was confirmed to be MK-4.

EXAMPLE 3

At first, 20 ml of a medium (pH 7.2) comprising 5% glycerol, sucrose or glucose, 1% peptone, 0.5% yeast extract, and 1% corn steep liquor was placed in a 300 ml-Erlenmeyer flask provided with baffles, and sterilized at 120° C. for 15 minutes. One loopful of each slant culture on a bouillon agar medium at 30° C. for 24 hours, shown in Table 1 was inoculated therein, and calcium carbonate separately sterilized by dry heating was added thereto to make 2% concentration. The microorganism was then cultured at 30° C. with shaking at 200 rpm, and the content of MK-4 in the culture broth after 5 days is shown in Table 1.

TABLE 1

| Strain | Carbon source* | MK-4 (mg/l) |
|---|---|---|
| *Arthrobacter nicotianae* ATCC 14929 | B | 7.2 |
| *Corynebacterium aquaticum* ATCC 14665 | A | 3.5 |
| *Corynebacterium murisepticum* ATCC 21374 | B | 2.5 |
| *Corynebacterium choliniphilum* NRRL B-11157 | B | 2.8 |
| *Microbacterium lacticum* ATCC 8180 | C | 15.0 |
| *Microbacterium imperiale* ATCC 8365 | C | 4.5 |
| *Microbacterium arborescens* ATCC 4358 | B | 8.6 |
| *Curtobacterium citreum* ATCC 15828 | C | 3.6 |
| *Aureobacterium testaceum* ATCC 15829 | B | 10.5 |
| *Brevibacterium fuscum* IFO 12127 | C | 4.0 |
| *Brevibacterium linens* ATCC 9175 | C | 2.4 |
| *Flavobacterium marinotypicum* ATCC 19260 | B | 12.0 |
| *Flavobacterium flavescens* ATCC 8315 | B | 6.5 |

TABLE 1-continued

| Strain | Carbon source* | MK-4 (mg/l) |
|---|---|---|
| *Flavobacterium dehydrogenans* ATCC 13930 | C | 3.2 |

*A: glucose, B: sucrose, C: glycerol

EXAMPLE 4

In this step, 300 ml of a seed medium (pH 7.2) comprising 1 g/dl peptone, 1 g/dl meat extract and 0.3 g/dl NaCl was placed into a 2 l-Erlenmeyer flask and sterilized.

Then, *Arthrobacter nicotianae* KS-8-18 was inoculated on the medium and incubated with shaking at 28° C. for 24 hours. Then, 300 ml of the culture broth was transferred into a 5 l-jar fermenter containing 3 l of a fermentation medium having the following composition and cultured under such cultural conditions as at a rotation of 400 rpm, an aeration rate of 3 l/min and a temperature of 28° C. for 5 days.

The yield of MK-4 was 36 mg/l, and the yield of carotenoid was 55 mg/l. The cell extract showed dark reddish orange.

Then, 2 l of the culture broth was centrifuged, whereby 43 g by dry weight of the cells was obtained. Then, the cells were extracted three times with 400 ml of methanol at 55° C., and the extract was concentrated. The resulting oily matters were admixed with 250 ml of hexane and insoluble matters were removed by filtration. Then, 7 g of silica gel was added to the filtrate, and the mixture was stirred to adsorb MK-4 on the silica gel. After washing unadsorbed matters off, MK-4 was eluted with 50 ml of ethyl acetate. The eluate was concentrated under reduced pressure, whereby 120 mg of an oily matter was obtained.

Then, the oily matter was dissolved in 7 ml of acetone, and the acetone solution was spotted on TLC plates of silica gel 60 $F_{254}$ (made by Merck) (7 sheets) and developed with toluene-ethyl acetate (9:1 v/v). Portion showing an ultraviolet absorption of Rf 80 was scraped off, extracted with acetone, concentrated and dissolved again in 3.5 ml of acetone. The solution was spotted on TLC plates of silica gel 60 $F_{254}$ (made by Merck) (7 sheets) impregnated with paraffins in advance and developed with acetone:water (95:5 v/v), and a portion of Rf 62 coincident with the standard product of MK-4 was scraped off, extracted with acetone, and concentrated, whereby 30 mg of MK-4 was obtained.

This substance was confirmed to be MK-4 by reversed phase thin layer chromatography, high pressure liquid chromatography, etc.

On the other hand, *Arthrobacter nicotianae* ATCC 14929 was cultured in a fermentation medium (pH 7.2) comprising 3 g/dl sucrose, 2 g/dl yeast extract, 0.1 g/dl potassium dihydrogen phosphate, 0.05 g/dl dipotassium hydrogen phosphate, 0.1 g/dl magnesium sulfate, 0.25 g/dl ammonium sulfate, 0.5 g/dl calcium carbonate and 0.1 mg/dl ferrous sulfate under the same conditions as mentioned above. In this case, the yield of MK-4 was 5.3 mg/l, the cell extract solution showed light yellow, and 1 mg/l carotenoid was by-produced.

As is obvious from the foregoing, the present carotenoid pigment-producing mutant produces a very considerble amount of carotenoid and at the same time produces a very considerable amount of MK-4, as compared with the parent strain.

What is claimed is:

1. A process for producing menaquinone-4 which comprises culturing, in a nutrient medium, a microorganism capable of producing menaquinone-4 selected from the group consisting of *Arthrobacter nicotianae* (ATCC 14929), *Corynebacterium aquaticum* (ATCC 14665), *Corynebacterium choliniphilium* (NRRL B-11157), *Corynebacterium murisepticum* (ATCC 21374), *Microbacterium lacticum* (ATCC8180), *Microbacterium imperiale* (ATCC 8365), *Microbacterium arborescens* (ATCC 4358), *Curtobacterium citreum* (ATCC 15828), *Aureobacterium testaceum* (ATCC 15829), *Brevibacterium fuscum* (IFO 12127), *Brevibacterium linens* (ATCC 9175), *Flavobacterium marinotypicum* (ATCC 19260), *Flavobacterium flavescens* (ATCC 8315) and *Flavorbacterium dehydrogenans* (ATCC 13930) until menaquinone-4 is accumulated in the culture broth and recovering menaquinone-4 therefrom.

2. A process for producing menaquinone-4 which comprises culturing the carotenoid pigment-producing mutant strain, *Arthrobacter nicotianae* KS-8-18 (FERM BP-1022) in a nutrient medium until menaquinone-4 is accumulated in the culture broth and recovering the menaquinone-4 therefrom.

* * * * *